US006695773B1

(12) United States Patent
Dahlinger

(10) Patent No.: US 6,695,773 B1
(45) Date of Patent: Feb. 24, 2004

(54) SURGICAL INSTRUMENT FLUID SHIELD

(76) Inventor: Eric Dahlinger, 181 Meadowlark Dr., Hawthorn Woods, IL (US) 60047

( * ) Notice: Subject to any disclaimer, the term of this patent is extended or adjusted under 35 U.S.C. 154(b) by 0 days.

(21) Appl. No.: 10/113,155

(22) Filed: Apr. 1, 2002

Related U.S. Application Data

(60) Provisional application No. 60/323,556, filed on Sep. 20, 2001.

(51) Int. Cl.$^7$ ................................................. A61B 1/00
(52) U.S. Cl. ....................................... 600/119; 128/857
(58) Field of Search ................................ 600/119, 186; 604/268; 128/852, 853, 857

(56) References Cited

U.S. PATENT DOCUMENTS

| | | | | |
|---|---|---|---|---|
| 3,144,020 A | * | 8/1964 | Zingale | ....................... 600/119 |
| 4,657,020 A | | 4/1987 | Lifton | |
| 4,834,068 A | | 5/1989 | Gottesman | |
| 4,958,623 A | * | 9/1990 | Rocco | ....................... 600/119 |
| 4,976,254 A | | 12/1990 | Dash et al. | |
| 5,123,402 A | | 6/1992 | Vandenbossche et al. | |
| 5,496,290 A | * | 3/1996 | Ackerman | ................... 604/268 |
| 5,947,894 A | * | 9/1999 | Chapman et al. | ........... 600/119 |
| 6,402,724 B1 | * | 6/2002 | Smith et al. | ................. 604/289 |

* cited by examiner

Primary Examiner—John P. Leubecker
(74) Attorney, Agent, or Firm—Hayes Soloway PC

(57) ABSTRACT

A surgical instrument fluid shield is disclosed having a radially proximal edge, at least a portion thereof defining an adjustable aperture for engaging an elongated object, and a conical-shaped section which opens outward from the radially proximal edge, to a wider radially peripheral edge. A portion of the adjustable aperture preferably is in the shape of a sleeve or the like which sealingly engages the elongated object, forming a generally fluid tight seal between the shield and the elongated object and helping to maintain proper alignment of the shield while on the endoscope or other device. The shield may be made of a rubber material such as silicone or a biocompatible elastomer material. The shield may be sufficiently stiff to generally maintain its shape while being simultaneously resilient to allow the aperture at the radially proximal edge to adjust to the outside dimension of the elongated object. The peripheral edge of the conical shield has an outward extending lip which further deflects the splash or flow of fluid away e.g., from the instrument eyepiece, camera coupler, and face and hands of the surgeon during a procedure.

21 Claims, 2 Drawing Sheets

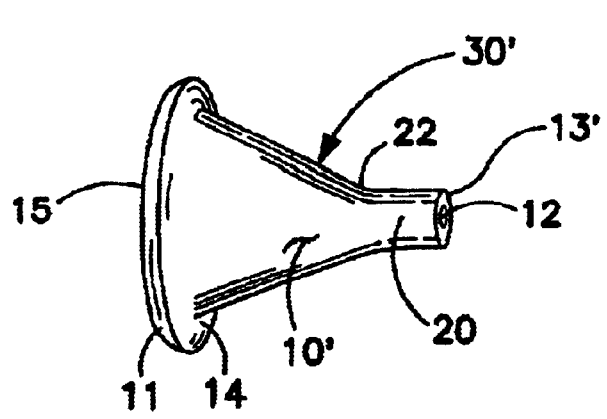
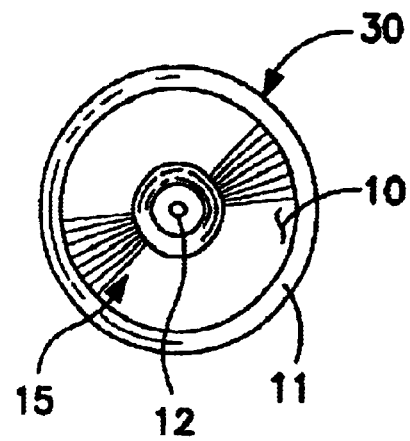
FIG. 5
FIG. 6c
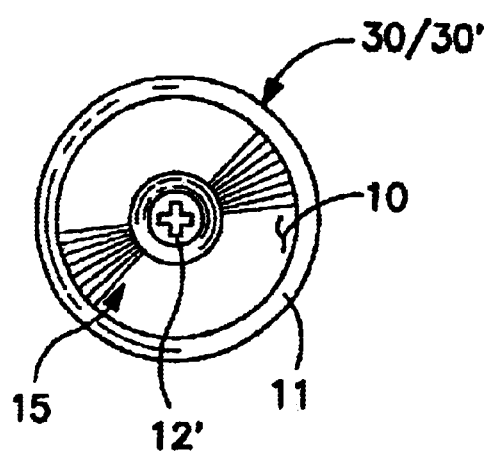
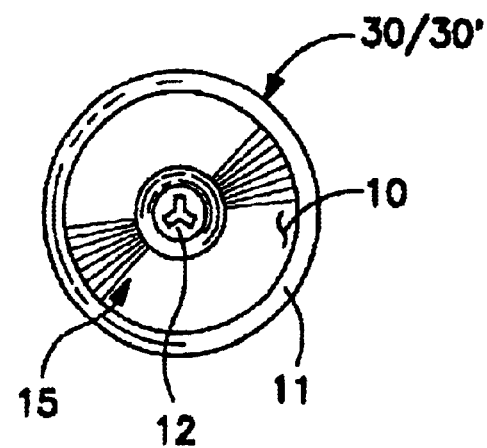
FIG. 6a
FIG. 6b

SURGICAL INSTRUMENT FLUID SHIELD

CROSS-REFERENCE TO RELATED APPLICATIONS

This application claims the benefit of copending U.S. provisional patent application Ser. No. 60/323,556 filed Sep. 20, 2001, the teachings of which are incorporated by reference.

FIELD OF THE INVENTION

The present invention relates generally to a surgical device and more particularly to a shield for use with a surgical instrument to prevent fluid splash back. The invention has particular utility for use in connection with an endoscope or other elongated optical-medical device to prevent fluid flow or fogging of the endoscope eyepiece or video camera/coupler interface, and will be described in connection with such utility, although other utilities are contemplated.

BACKGROUND OF THE INVENTION

Medical science has long sought ways to minimize the dangers and trauma inherent in invasive surgical procedures. To this end, surgical techniques and instruments have been developed which, among other things, reduce the size of the incisions required to perform various surgical procedures. These techniques and instruments have been remarkably successful. Procedures that only a few years ago would require an incision of several inches in length, are today being performed through incisions which are less than one inch in length.

Surgical instruments such as trocars, cannulas and optical medical devices (endoscopes), such as cystoscopes, arthroscopes, laparoscopes, etc., are inserted through small incisions or openings in a patient's body or body cavity and manipulated to perform surgical procedures within the patient's body or body cavity. The optical medical devices generally include an optical pathway adjacent to an eyepiece. When using these instruments, blood or other body fluids, or irrigating fluids may drain or leak through the incision or cavity around the instrument so as to splash the face of the endoscopist, and/or flow onto or fog the eyepiece, thus compromising visibility, or otherwise interfere with the procedure.

Various cumbersome shield devices have been proposed in the art. For example, a large, rigid plastic shield mounted on an endoscope sized to vertically extend and cover the length of the user's face and horizontally, to cover the sides of the face of the user is shown in U.S. Pat. No. 4,976,254 to Dash, et al. A generally flat rigid plastic shield, about 12 inches in diameter, having a cylindrical collar adapted to fit onto the boss of the surgical instrument, and secured thereto via clamp assembly or vinyl tape is described in U.S. Pat. No. 5,123,402 to Vandenbossche, et al. A similar disc shaped, rigid plastic splash shield, about 6–12 inches in diameter, having a circular frame made of wire or plastic connected to the outer circumference of the shield to provide support and maintain the shape of the shield, is disclosed in U.S. Pat. No. 4,834,068 to Gottesman. A latex bell-shaped hood for preventing damage to the passage tract or cavity of the patient's body caused by a foreign object upon removal taught in U.S. Pat. No. 4,657,020 to Lifton does not provide protection of the face of the endoscopist or the eyepiece of the instrument from the splash or flow of fluid during a procedure. None of these above prior art devices have proved to be particularly effective or convenient to use.

Therefore a need has arisen for a surgical access device that overcomes the above-noted problems. The present invention fulfills these needs and provides other related advantages.

SUMMARY OF THE INVENTION

It is an object of the present invention to provide a device to deflect unwanted and uncontrolled fluid flow from exiting the patient and flowing or splashing onto the instrument eyepiece, camera coupler, and face and hands of the surgeon during endoscopic procedures, that is simple, inexpensive, flexible and relatively compact, and will accommodate a variety of diameters and instruments and does not need to be specifically made or modified to a particular piece, thereby reducing the need for inventory of numerous sized individual units. The device can even be inserted backwards or inverted and still accomplish the aforementioned objectives.

It is another object of the present invention to provide a device that does not require special coupling hardware and can be slid quickly and easily onto or off of any portion of length of instrument depending on situation or preference, helping to ensure that the operation will not be delayed due to fogging, or that surgical outcome is not compromised due to lack of visibility, including visibility within a cavity or that the procedure may be compromised or delayed due to excessive leakage of distention media.

In one embodiment, the present invention provides an adaptable conical shield for frictionally engaging an elongated object of various diameters, such as an endoscope or other surgical instrument, comprising a radially proximal edge, at least a portion thereof defining an adjustable aperture for engaging said elongated object, a conical-shaped section which opens outward from said radially proximal edge, to a wider radially peripheral edge. Further, a portion of the adjustable aperture may be in the shape of a sleeve which sealingly engages the elongated object, forming a generally fluid tight seal between the shield and the elongated object and helps maintain proper alignment of the shield while on the endoscope or other device. Preferably, the conical shield is comprised of rubber material such as silicone, but other biocompatible elastomer materials may be used. Alternatively, other self-sealing membraneous materials may be used. Preferably, the shield is sufficiently stiff to generally maintain its shape while being simultaneously resilient to allow the aperture at the radially proximal edge to adjust to the outside dimension of the elongated object. The peripheral edge of the conical shield may have an outward extending lip which further deflects the splash or flow of fluid away from the instrument eyepiece, camera coupler, and face and hands of the surgeon during a procedure.

In use the shield of the present invention is installed on the surgical instrument or elongated object simply by sliding the adjustable aperture onto the instrument and then conveniently positioning the shield between the eyepiece and the incision in the patient's body or the body cavity according to the procedure and the user's preference. Similarly, the shield is easily repositioned, removed or replaced. Various instruments or endoscopes used on a procedure may be fitted with their own shield to reduce time and inconvenience of moving a unit. The device may be designed and manufactured of materials that render it as single-use or multiple use.

The present invention provides a shield for use with an elongated object such as a surgical instrument. The shield has a first radial edge portion, a second radial edge portion, and a center section opening outward from the first radial edge portion and joining the second radial edge portion. The first radial edge portion having an aperture for frictionally and sealingly engaging the elongated object and the second radial edge portion being greater in dimension than the first radial edge.

Other features and advantages of the present invention will become apparent as the following Detailed Description proceeds, and upon reference to the Drawings, wherein like numerals depict like parts, and wherein:

BRIEF DESCRIPTION OF THE DRAWINGS

FIG. 5 is a perspective view of another exemplary surgical instrument shield device consistent with the present invention; and FIGS. 6(a)–6(c) are plan views showing alternative aperture options.

DETAILED DESCRIPTION OF THE PREFERRED EMBODIMENT

Figure 1:
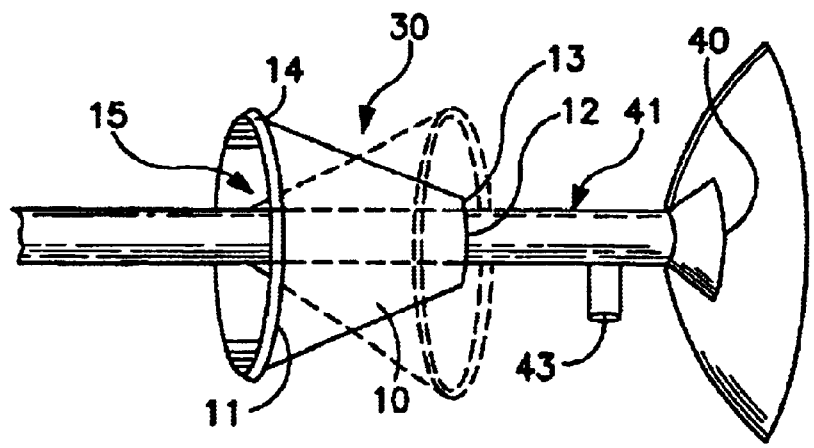
FIG. 1 is a perspective view of an exemplary surgical instrument shield device consistent with the present invention.
Figure 2:
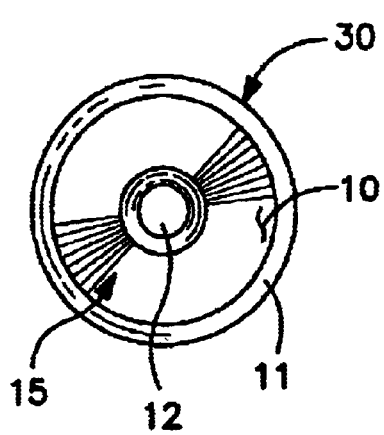
FIG. 2 is a plan view of the open front end of the surgical instrument shield device of FIG. 1.
Figure 3:
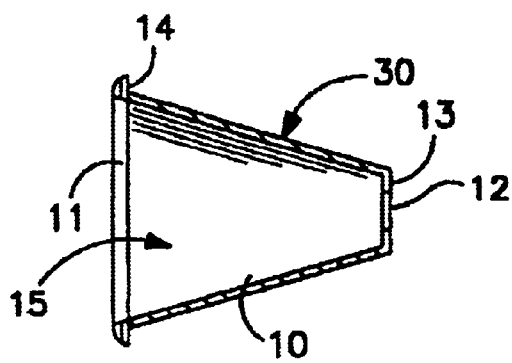
FIG. 3 is a cross-sectional side view of the surgical instrument shield device of FIG. 1.
Figure 4:
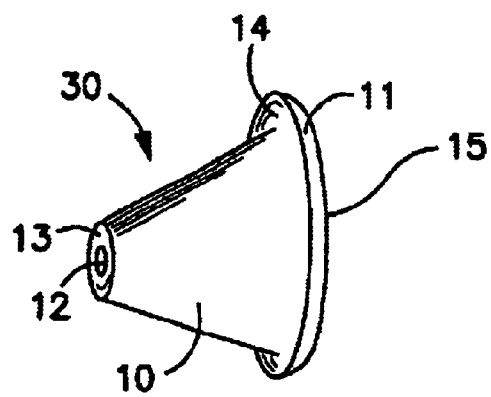
FIG. 4 is a perspective view showing the back end of the surgical instrument shield of FIG. 1.

Referring to FIGS. 1–4, an exemplary surgical instrument shield device 30 is shown mounted on endoscope 41. In the preferred embodiment, the surgical instrument shield device 30 is generally conical in shape, comprising a radially proximal edge 13 having a generally circular aperture 12 (see FIG. 6c) located centrally therein for being sealingly mounted on and frictionally engaging the endoscope 41. The aperture 12 is preferably adjustable, the adjustable aperture 12 in the relaxed state is smaller in dimension than the outside dimension of the elongated object onto which it is to be installed. Preferably, surgical instrument shield 30 is comprised of a medically acceptable resiliently flexible material such as silicone. Alternatively, other biocompatible elastomer or self-sealing membraneous materials may be used. All or part of shield 30 may be clear, opaque or colored to meet market needs. Preferably, the shield 30 is sufficiently stiff to maintain generally its conical shape while being simultaneously resilient to allow the aperture 12 at the radially proximal edge 13 to adjust to the outside dimension of the endoscope 41 or other elongated object.

The shield 30 further includes a conical-shaped section 10 that opens outward from radially proximal edge 13 forming an open mouth area 15. The open mouth area 15 may face towards the patient for blocking the flow or splash of fluid from the user looking through an eyepiece 40 of the endoscope 41. In this embodiment, a peripheral edge 11 includes a lip portion 14 that opens radially outward and curves away from open mouth area 15, said lip portion 14 adding strength to the peripheral edge 11 and to further deflect fluid away from the user. Alternatively, the shield device 30 may be reversed in position, i.e. with the open mouth area 15 facing away from the patient as shown in phantom in FIG. 1. Of course, shield 30 may vary in shape and dimension. For example, the shield 30 may be in the shape of a bell or dish-shaped, and the diameter or dimension of the peripheral edge may be only slightly larger than the elongated object onto which it is mounted.

Referring to FIG. 5, another exemplary surgical instrument shield device 30' is shown. A cylindrical shaped sleeve 20 extending from a narrower portion 22 of a conical housing 10' of surgical instrument shield device 30' includes proximal end 13' and adjustable aperture 12 for sealingly engaging an elongated object, forming a generally fluid tight seal between the shield 30' and the elongated object.

In use, the surgical instrument shield device 30/30' may be installed on the elongated object, for example an endoscope 41, as shown in FIG. 1, by slidably mounting adjustable aperture 12 onto said elongated object. The shield 30/30' may then be positioned along the length of the elongated object between the eyepiece 40 or a light source 43 and the incision in the patient's body or the body cavity according to the procedure and the user's preference. In this fashion, the shield 30/30' is frictionally held in place by adjustable aperture 12 and is easily repositioned, removed or replaced.

FIGS. 6(a) and 6(b) illustrate alternative aperture shapes 12' and 12" consistent with the present invention. However, other shapes also advantageously may be used.

A feature and advantage of the shield of the present invention is that the shield can be used internally to facilitate control of heat or fluid flow from an operative site. For example, the shield can be inserted in closed position, and then opened like an umbrella and positioned over an operative site. One particular application would be for arthroscopic capsular shrinkage with RF wand or thermal probe. Hot distension media is not good for surrounding tissue so it could be captured, controlled and removed via suction, etc.

Another feature and advantage of the present invention is that the shield helps to hold fluid in place in the body cavity, which helps dissipate heat and thus prevent tissue damage to surrounding tissue. Still other features and advantages will become clear from the use of the invention.

Various modifications and variations of the present invention are possible in light of the above teaching. It is, therefore, to be understood that within the scope of the appended claims, the invention may be practiced otherwise than literally described, but fall within the scope therein.

What is claimed is:

1. A surgical instrument fluid shield comprising:
   a first radial edge portion, the radial edge portion having an aperture for frictionally and sealingly engaging an elongated object;
   a second radial edge portion having a lip portion at a distal end that opens radially outward and curves away from the second radial edge portion, the second radial edge portion being greater in dimension than the first radial edge portion; and
   a center section opening outward from the first radial edge portion and joining the second radial edge portion.

2. The shield of claim 1, wherein the center section is generally conical.

3. The shield of claim 1, wherein the center section is bell-shaped or dish-shaped.

4. The shield of claim 1, wherein the lip portion is shaped to deflect fluid radially away from the elongated object so as not to splash a user looking down a longitudinal axis of the elongated object from the second radial edge portion towards the first radial edge portion.

5. The shield of claim 1, wherein the aperture is located centrally on the first radial edge portion.

6. The shield of claim 1, wherein the aperture has an adjustable diameter.

7. The shield of claim 1, wherein the aperture is circular or cross-haired.

8. The shield of claim 1, wherein the aperture is smaller in dimension than the outside dimension of the elongated object onto which it is to be installed.

9. The shield of claim 1, wherein the shield is comprised of a resiliently flexible material.

10. The shield of claim 9, wherein the resiliently flexible material is a silicone.

11. The shield of claim 1, wherein the shield is comprised of an elastomer.

12. The shield of claim 11, wherein elastomer is biocompatible.

13. The shield of claim 1, wherein the shield is comprised of a self-sealing membrane.

14. The shield of claim 1, wherein the shield further comprises a cylindrical shaped sleeve extending from the first radial edge portion.

15. The shield of claim 1, wherein the lip portion redirects fluid radially outward and away from the second radial edge portion.

16. The shield of claim 1, wherein the shield is comprised of a resiliently flexible material offering memory properties.

17. A method of preventing fluid from exiting an opening formed in a patient and splashing on a user, comprising the steps of:

obtaining a shield having a first end with an aperture for sealingly engaging an outside surface of a surgical instrument and a second end that is greater in dimension than the first end;

sliding the second end of the shield over a distal end of a surgical instrument;

passing the distal end of the surgical instrument through the aperture at the first end of the shield; and reversing the orientation of the shield on the surgical instrument without removing the shield from the surgical instrument such that the second end is in closer proximity to the distal end of the surgical instrument than the first end of the surgical instrument.

18. A surgical instrument fluid shield comprising:

a first radial edge portion, the radial edge portion having an aperture for frictionally and sealingly engaging an elongated object;

a second radial edge portion having a lip portion that opens radially outward and curves away from a user looking down a longitudinal axis of the elongated object from the second radial edge portion towards the first radial edge portion, the second radial edge portion being greater in dimension than the first radial edge portion; and a center section opening outward from the first radial edge portion and joining the second radial edge portion.

19. The surgical instrument fluid shield of claim 18, wherein the center section is bell-shaped or dish-shaped.

20. The surgical instrument fluid shield of claim 18, wherein the surgical instrument fluid shield is comprised of a resiliently flexible material.

21. The surgical instrument fluid shield of claim 18, wherein the shield further comprises a cylindrical shaped sleeve extending from the first radial edge portion.

* * * * *